US008147410B2

United States Patent
Zheng

(10) Patent No.: US 8,147,410 B2
(45) Date of Patent: Apr. 3, 2012

(54) METHOD AND APPARATUS FOR ULTRASOUND IMAGING AND ELASTICITY MEASUREMENT

(75) Inventor: Yongping Zheng, Kowloon (HK)

(73) Assignee: The Hong Kong Polytechnic University, Hung Hom, Kowloon (HK)

( * ) Notice: Subject to any disclaimer, the term of this patent is extended or adjusted under 35 U.S.C. 154(b) by 397 days.

(21) Appl. No.: 12/382,699

(22) Filed: Mar. 23, 2009

(65) Prior Publication Data

US 2010/0240994 A1 Sep. 23, 2010

(51) Int. Cl.
*A61B 8/00* (2006.01)

(52) U.S. Cl. ........ 600/438; 600/437; 600/443; 600/447; 600/454; 382/128

(58) Field of Classification Search .................. None
See application file for complete search history.

(56) References Cited

U.S. PATENT DOCUMENTS

| | | |
|---|---|---|
| 4,947,851 A | 8/1990 | Sarvazyan et al. |
| 5,099,848 A | 3/1992 | Parker et al. |
| 5,107,837 A | 4/1992 | Ophir et al. |
| 5,115,808 A * | 5/1992 | Popovic et al. ............... 600/438 |
| 5,178,147 A * | 1/1993 | Ophir et al. .................... 600/437 |
| 5,606,971 A * | 3/1997 | Sarvazyan ..................... 600/438 |
| 6,350,238 B1 * | 2/2002 | Olstad et al. .................. 600/437 |
| 6,371,912 B1 | 4/2002 | Nightingale et al. |
| 6,494,840 B1 | 12/2002 | Mak et al. |
| 6,561,981 B2 * | 5/2003 | Bonnefous ..................... 600/443 |
| 6,770,033 B1 | 8/2004 | Fink et al. |
| 7,252,004 B2 * | 8/2007 | Fink et al. ......................... 73/597 |
| 7,444,875 B1 * | 11/2008 | Wu et al. .......................... 73/602 |
| 7,678,051 B2 * | 3/2010 | Fan et al. ....................... 600/438 |

\* cited by examiner

*Primary Examiner* — Long V. Le
*Assistant Examiner* — Nicholas Evoy
(74) *Attorney, Agent, or Firm* — The Hong Kong Polytechnic University

(57) ABSTRACT

A method for performing ultrasound imaging and elasticity measurement, the method includes scanning an object to obtain a B-mode ultrasound image, selecting an A-mode signal from the B-mode ultrasound image, transmitting a high frame rate ultrasound signal, by a selected group of ultrasound transducers, at the selected A-mode signal location, forming a transient M-mode image based on the high frame rate ultrasound signal, enhancing propagation trace of shear wave based on the transient M-mode image, calculating elasticity of the object based on the propagation trace and displaying result, and displaying, simultaneously, the B-mode ultrasound image and the transient M-mode measurement result.

10 Claims, 8 Drawing Sheets

METHOD AND APPARATUS FOR ULTRASOUND IMAGING AND ELASTICITY MEASUREMENT

BACKGROUND OF THE INVENTION

1. Field of the Invention

The present invention is related to ultrasound imaging and elasticity measurement for conventional ultrasound scanners.

2. Description of the Related Art

The measurement of tissue elasticity is very important in different clinical fields, such as assessment of liver fibrosis caused by various liver disease, scarring caused by burn, tissue fibrosis caused by radiotherapy, muscle stiffening caused by contraction and fatigue, etc. Consequently, various techniques for measuring tissue elasticity have been developed, for example, U.S. Pat. No. 6,494,840 teaches a tissue palpation device based on ultrasound indentation technique for quantitative measurement of tissue elasticity. By using an ultrasound imaging probe together with ultrasound indentation measurement, tissue elasticity can be measured with the guide of ultrasound imaging.

However, the palpation device has a number of limitations, including the requirement of tissue boundary condition. For instance, tissue needs to be directly compressed and requires an underlying tissue boundary. Also, the device can only provide an average elasticity valued for the entire tissue being compressed.

Another technique has been developed using static compression to show elasticity distribution in the tissue using strain imaging, for example, as disclosed in U.S. Pat. No. 5,107,837. Also, another technique has been developed using a vibration source and Doppler tissue velocity detection to map elasticity distribution, as discussed in U.S. Pat. No. 5,099,848. Furthermore, a number of approaches have been developed that uses vibration or acoustic radiation force to generate shear waves in tissues while using high frame rate ultrasound to monitor the propagation of the shear wave so as to measure or image tissue elasticity.

By using the foregoing methods, using vibration and radiation force, the intrinsic values of elasticity such as Young's modulus can be measured. However, there is still a need for simultaneous elasticity measurement and ultrasound imaging using conventional ultrasound imaging device.

SUMMARY OF THE INVENTION

According to an aspect of the present invention, A method for performing ultrasound imaging and elasticity measurement, the method includes scanning an object to obtain a B-mode ultrasound image, selecting an A-mode signal from the B-mode ultrasound image, transmitting a high frame rate ultrasound signal, by a selected group of ultrasound transducers, at the selected A-mode signal location, forming a transient M-mode image based on the high frame rate ultrasound signal, enhancing propagation trace of shear wave based on the transient M-mode image, calculating elasticity of the object based on the propagation trace and displaying result, and displaying, simultaneously, the B-mode ultrasound image and the transient M-mode measurement result.

According to another aspect of the present invention, an imaging apparatus for performing ultrasound imaging and elasticity measurement, includes a scan control unit configured to scan an object to obtain a B-mode ultrasound image, a selecting unit configured to select an A-mode signal from the B-mode ultrasound image, an ultrasound probe configured to transmit a high frame rate ultrasound signal, by a selected group of ultrasound transducers, at the selected A-mode signal location, a processing unit configured to form a transient M-mode image based on the high frame rate ultrasound signal, an enhancing unit configured to enhance propagation trace of shear wave based on the transient M-mode image, a calculating unit configured to calculate elasticity of the object based on the propagation trace and displaying result, and a display unit configured to display, simultaneously, the B-mode ultrasound image and the transient M-mode measurement result.

Further features and aspects of the present invention will become apparent from the following description of exemplary embodiments with reference to the attached drawings.

DESCRIPTION OF THE EMBODIMENTS

Various embodiments of the present invention will be described in detail hereinafter with reference to the accompanying drawings.

Figure 1:
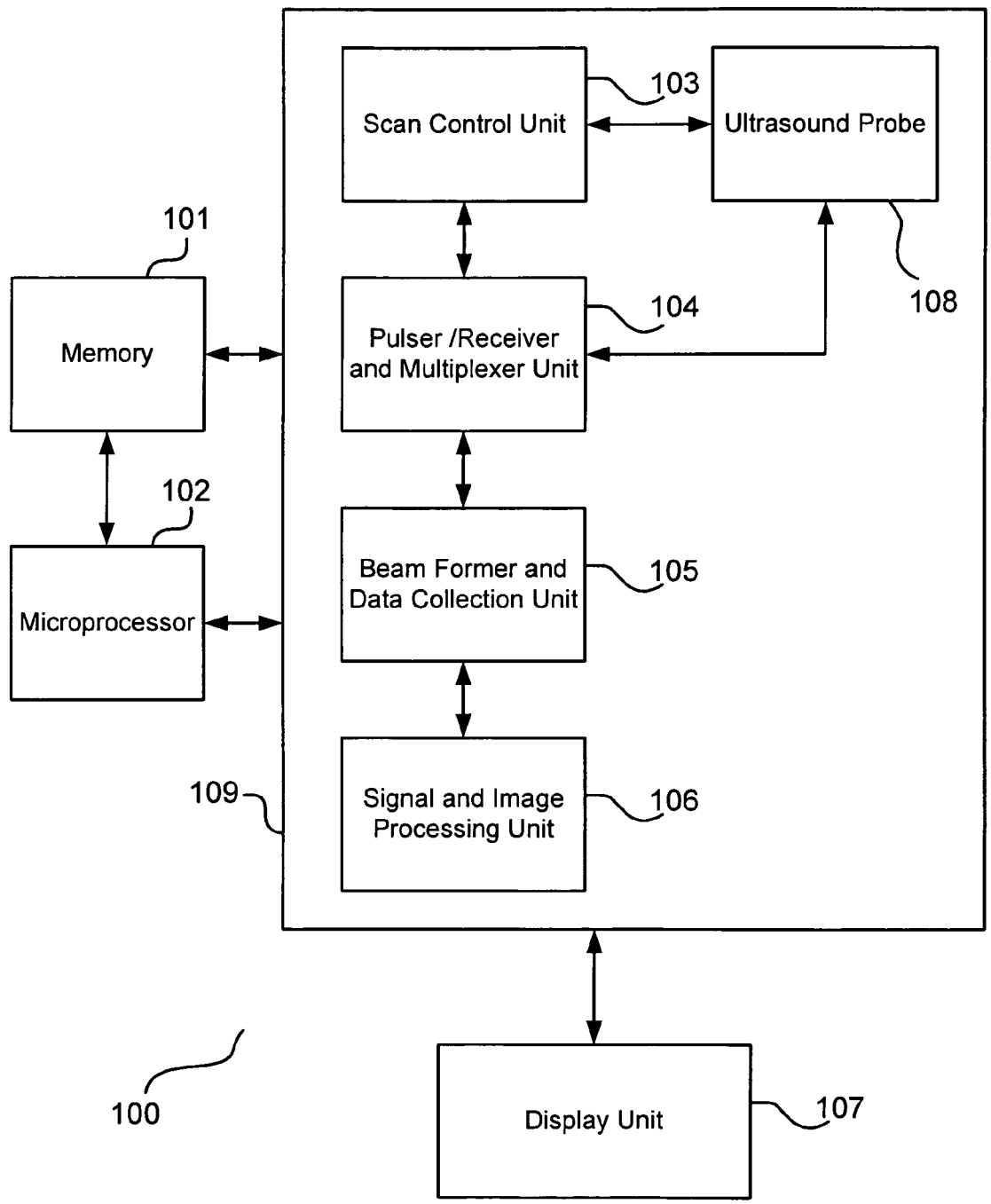
FIG. 1 is an exemplary block diagram of the hardware schematic of the present invention.

FIG. 1 is an exemplary block diagram of the hardware schematic of the present invention. Ultrasound scanning system 100 includes memory 101, microprocessor 102, ultrasound scanner 109, and display unit 107. The ultrasound scanner 109 includes a scan control unit 103, pulser/receiver and multiplexer unit 104, beam former unit 105, signal and image processing unit 106, and ultrasound probe 108. Each element in FIG. 1 is capable of communicating with another element in the ultrasound scanning system 100.

Microprocessor 102 is capable of executing instruction for controlling the ultrasound scanner 109. Microprocessor 102 may communicate with memory 101, which may include computer-executable program codes for driving the ultrasound scanner 109. The memory 101 serves as a main memory of the ultrasound system 100. The microprocessor 102 and memory 101 may be located in an external device such as a personal computer. In another embodiment, memory 101 and microprocessor 102 are embedded within the ultrasound scanner 109.

In a case of mechanical scanning, scanner control unit 103 controls the motor that is associated with the ultrasound probe 108 to execute scanning. Ultrasound probe 108 may include an array of ultrasound transducers, which will be described later with in connection with FIG. 2.

Scanner control unit controls pulser/receiver and multiplexer 104 generates timing pulse for driving the ultrasound transducers and performs electronic scanning. It is also capable of activating a selected subset of transducers from the ultrasound probe 108, and receiving signals from the ultrasound probe 108.

Beam former and data collection unit 105 generates appropriate delays for driving different elements of the array transducer and to collect ultrasound signals from different elements with different delay. Signal and image processing unit 106 processes the sequence of transient M-mode signals and determines tissue elasticity, which will be described in more detail below in connection with FIGS. 7A and 7B. It also processes beam formed signals to generate B-mode ultrasound images.

Display unit 107 displays the ultrasound image scanned by the ultrasound scanner. The display unit 106 may be an external display device such as a cathode ray tube (CRT) monitor or liquid crystal display (LCD) screen. The display unit may also be an LCD screen embedded on the ultrasound scanner.

Figure 2:
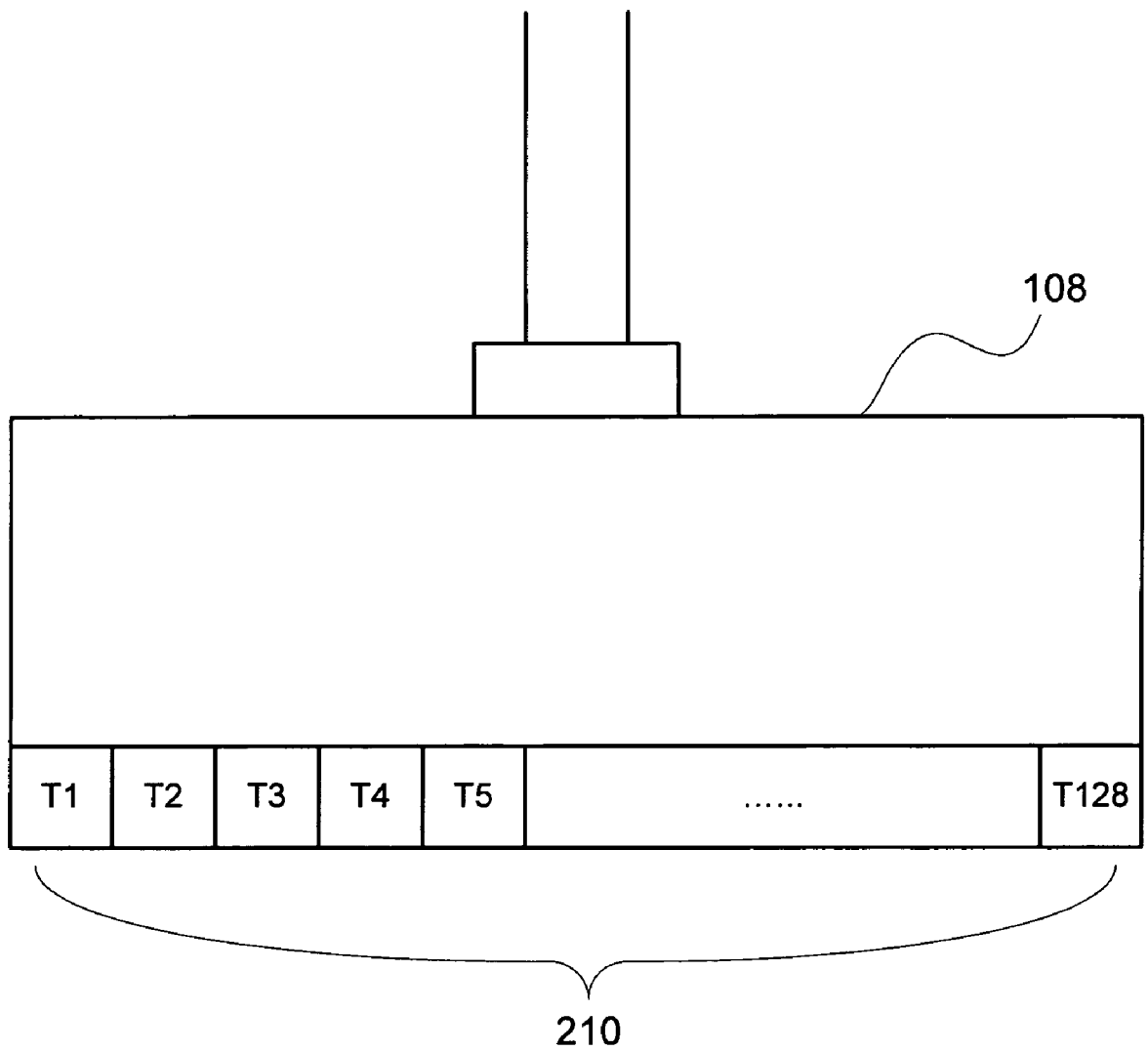
FIG. 2 shows an exemplary ultrasound probe configuration according to an embodiment of the present invention.

FIG. 2 illustrates the ultrasound probe 108 according to an embodiment of the present invention. The probe may be connected to the ultrasound scanner 109 via a flexible cable. As shown in FIG. 2, the ultrasound probe includes an array of ultrasound transducers 210. In this embodiment, 128 transducers are shown (T1 to T128). However, the present invention does not limit the number of ultrasound transducers to any specific number, any number of transducers may be utilized.

The ultrasound scanner 109 can work in two common modes. The first is to scan the ultrasound beam across the imaging plane to form an image of tissue (B-mode), and the second is to fix the ultrasound beam at certain location to continuously obtain ultrasound signal about the tissue along the beam (M-mode). For B-mode scanning, the scan of beam can be achieved using electronic scanning or mechanical scanning. For M-mode scanning, the obtained ultrasound signals can be drawn as time going to show any motion inside the tissue. The traditional M-mode used to view the motion of the heart and normally does not require a very high frame rate. The signals can also be used for the frequency analysis to obtain the local velocity of tissue, such as blood flow. This mode is called a Doppler's mode.

Figure 3:
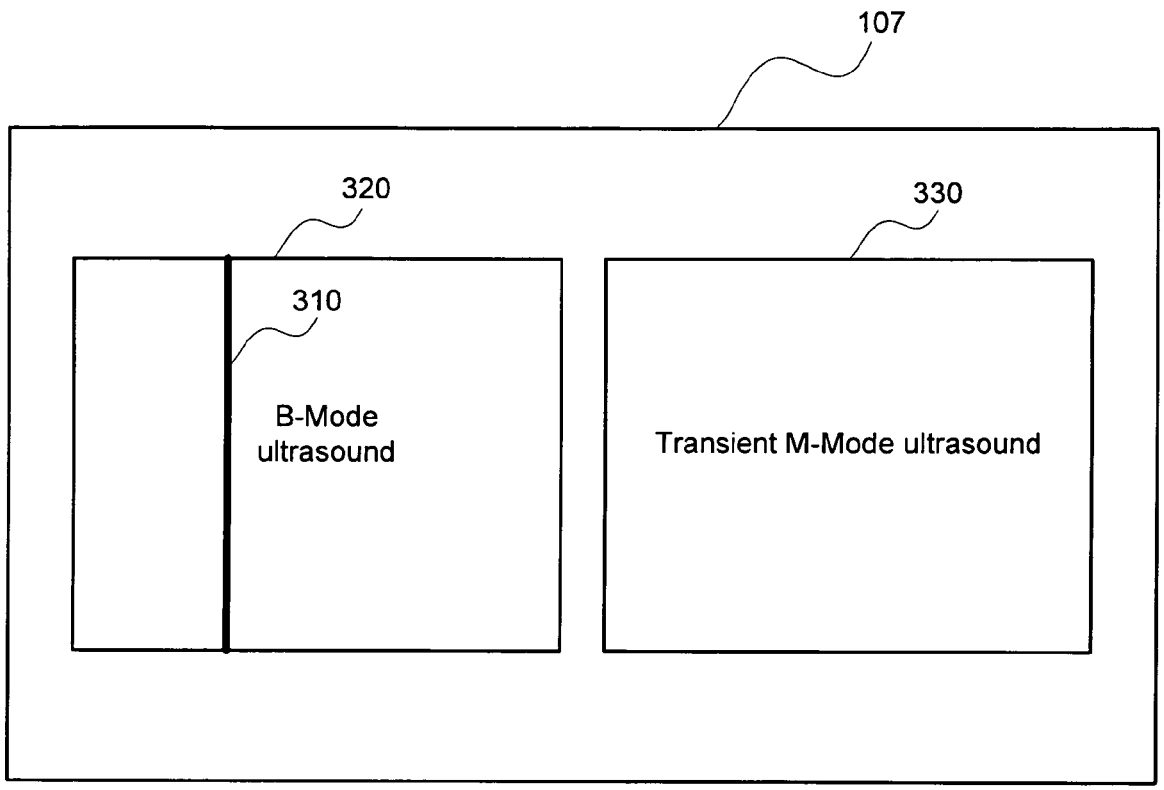
FIG. 3 shows an example for simultaneously displaying the B-mode image and transient M-mode image
Figure 7A:
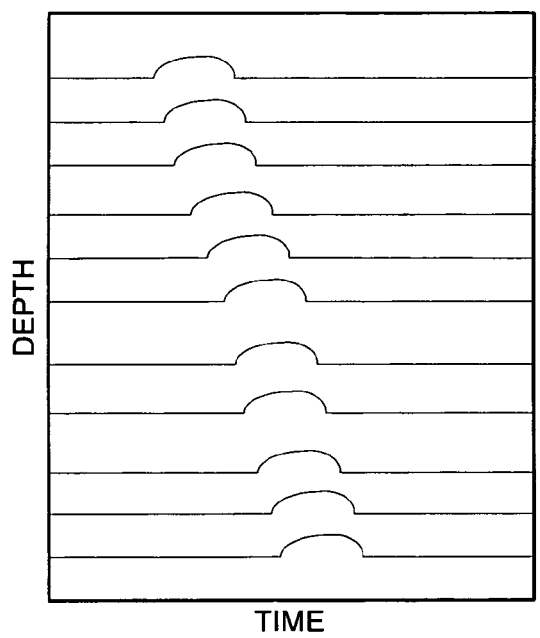
FIG. 7A shows a sequence of transient M-mode signals according to an embodiment of the present invention.

FIG. 3 shows simultaneous display of B-Mode 320 and transient M-mode 330 ultrasound images according to an embodiment of the present invention. The transient M-mode can be used to monitor the propagation of shear wave inside a tissue. If the tissue is homogeneous, the speed of shear wave is consistent at different depths and the trace will be a straight line. If the tissue is inhomogeneous, the trace of shear wave will be curved (FIG. 7A). In this regard, the propagation speed of shear wave in the tissue represents the stiffness or elastic modulus of the tissue.

The selecting line 310 in FIG. 3 can be controlled by the scan control unit 103 to automatically scan across the B-mode image. At each location of line 310, a transient M-mode ultrasound image can be obtained. The slope profile along the depth direction can be calculated for each location. Slope profiles at all locations can be used to form a map of slope. By calculating Young's modulus from the slope, a map of Young's modulus can also be formed.

According to mechanics and acoustics, the Young's modulus (for measuring tissue elasticity) can be calculated by the following equations:

$$c_s = \sqrt{\frac{G}{\rho}} \quad (1)$$

$$G = \frac{E}{2(1+v)} \quad (2)$$

Where $c_s$ is the propagation speed of shear wave in tissue, G is the shear modulus of tissue, $\rho$ is the tissue density, E is Young's modulus, and v is the Poisson's ratio of tissue. Since tissue is mainly comprised of water, it is nearly incompressible when it is compressed in a high enough compressing rate and its Poisson's ratio is close to 0.5 With this assumption, and we combine equations (1) and (2), we can have:

$$E = 3\rho c_s \quad (3)$$

Using Equation (3) and known tissue density, Young's modulus can be calculated using the speed of shear wave, which is measured using the transient M-mode. For certain tissue, such as liver, its density is relatively consistent. Hence, a constant value can be used.

If each the depth-dependent Young's modulus is concerned, the above calculation can be applied on slope of each segment of the shear wave trace. If the Young's modulus is depth-dependent, the trace 501 in FIG. 7B will not be a straight line. The trace can be represented by:

$$y = x(t) \quad (4)$$

The slope profile of the trace can be obtained by:

$$c_s(y) = y' = \frac{dx(t)}{dt} \quad (5)$$

where $c_s(y)$, i.e. the slope profile of the trace, represents the depth-dependent propagation speed of shear wave in tissue. Smoothing techniques, such as moving average or median filter, can be used to smooth the slope profile. The above calculation of the depth-dependent propagation speed of shear wave can be applied for all the selected location where the transient M-mode image is formed. Hence, a 2D map of propagation speed of shear wave, i.e. the slope of trace, can be obtained, which can be represented by $c_s(x,y)$, where x represents the lateral dimension and y represents the depth direction. Using $c_s(x,y)$ and equation (3), a map of Young's modulus can be calculated.

The ultrasound scanner 109 performs B-mode scanning at a rate of approximately 30 frames/sec. While performing B-mode scanning, a specific location of interest, such as line 310 can be selected. By selecting a specific location of interest, a subset of transducers is consequently selected for performing transient M-mode scanning. As an example, the subset of transducers may include 32 transducers (i.e. T33 to T64). Next, the frame rate for firing the subset of transducers is increased to collect ultrasound signals at the location of interest (a fixed location) to form a transient M-mode image, at least 1000 frames/sec. By sequentially switching between B-mode and transient M-mode scanning, B-mode ultrasound image can be viewed simultaneously with the transient M-mode.

The high frame rate can be applied to monitor the tissue disturbances, which can be generated using a number of methods, for example, by vibration or impact applied outside of the body or generated inside of the body (e.g. heart pulsation), acoustic radiation force generated by a focused ultrasound beam, a vibrating needle inserted inside the tissue, or voluntary or electrical stimulated muscle contraction, etc. Generally, mechanical shear wave can be induced by vibration, impact, heart pulsation, muscle contraction, or acoustic radiation force, etc. Shear wave propagates in tissue with a much slower speed in comparison with longitudinal wave used by ultrasound imaging. Thus, the transient M-mode ultrasound can view the propagation of shear wave inside the tissue.

In conventional M-mode, there is no synchronization for viewing M-mode, i.e. M-mode image is continuously formed frame-by-frame using available A-mode ultrasound signal. The starting point of each M-mode frame does not have any synchronization with other information. Conventionally, when M-mode is used to view heart tissues, ECG signal also be recorded and added on top of the M-mode image for reference. However, ECG signal is not used to synchronize the M-mode image. In this invention, transient M-mode ultrasound image is synchronized with the start of vibration, impact or acoustic radiation force disturbance to the tissue. Therefore, the transient M-mode images collected during repeated disturbances can be shown in a steady way on the screen.

There are two approaches to synchronize the transient M-mode images with the signals of disturbance. In the first case, the start of disturbance can be controlled, including the case of externally applied vibration, impact or acoustic radiation force or electrical stimulation applied for muscle contraction. Under this situation, a trigger signal can be generated by the ultrasound scanner to control the modules for generating vibration, impact, acoustic radiation force, or electrical stimulation for muscle contraction at this triggering moment. This same trigger signal can also be used to control the transient M-mode to start its scanning. Therefore, the transient M-mode image and the disturbance can be synchronized. To view the most beginning activities after the disturbance, the trigger signal can be sent to start the transient M-mode scanning and after certain time delay or before certain time in advance. In addition, to view the actual disturbance on the tissue, a motion sensor, such as accelerometer can be attached on the tissue surface to collection a signal related to the disturbance. This signal can be overlaid in the transient M-mode image.

In another embodiment, the start of disturbance cannot be controlled, such as the heart pulsation, voluntary muscle contraction, and manual impact on the tissue by a finger or a device. Under these situations, we can use a sensor to pick up the disturbance signal from the body surface and to use it as a trigger signal to start the transient M-mode scanning. The above-mentioned sensor can be an accelerometer to detect the movement of the tissue. The start of the tissue movement, as indicated by the acceleration can be used for triggering. Meanwhile, the disturbance signal collection by the motion sensor can also be displayed in the transient M-mode image for reference.

In the traditional M-mode ultrasound image, only envelope A-mode signals are used to form M-mode image. Therefore the phase information of the ultrasound signals has not been preserved. In the transient M-mode, radiofrequency (RF) data are used to form image and subsequent image processing is based on the RF data.

Figure 5:
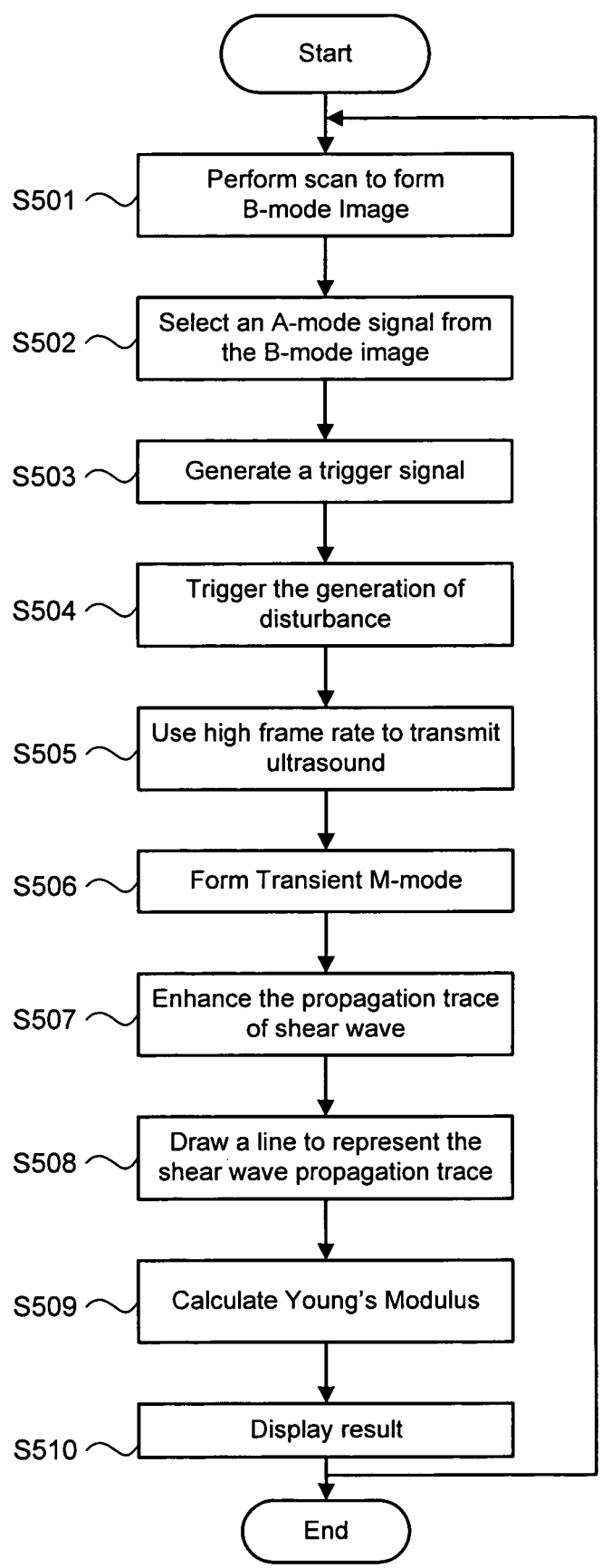
FIG. 5 shows an exemplary flow diagram for simultaneously displaying B-mode and transient M-mode ultrasound images.

FIG. 5 is a flowchart illustrating the process steps for simultaneously displaying B-Mode and transient M-mode ultrasound images. This approach can be applied for both mechanical and electrical ultrasound scanning. B-mode image and M-mode image are alternatively and continuously obtained for displaying.

In step S501, the ultrasound scanner 109 performs scanning to form a B-mode image. Then, the ultrasound scanner selects an A-mode signal from the B-mode image in step S502. In step S503, the ultrasound probe generates a trigger signal. Thereafter, the trigger signal controls the module for generating disturbance at the triggering moment (S504). The disturbance applied on the tissue should be electronically controllable, for instance, the disturbance may be triggered using a vibrator. In step S505, a high frame rate ultrasound signal beam is generated at the selected location. For example, a user may select a fixed location to focus the ultrasound signals.

Figure 4:
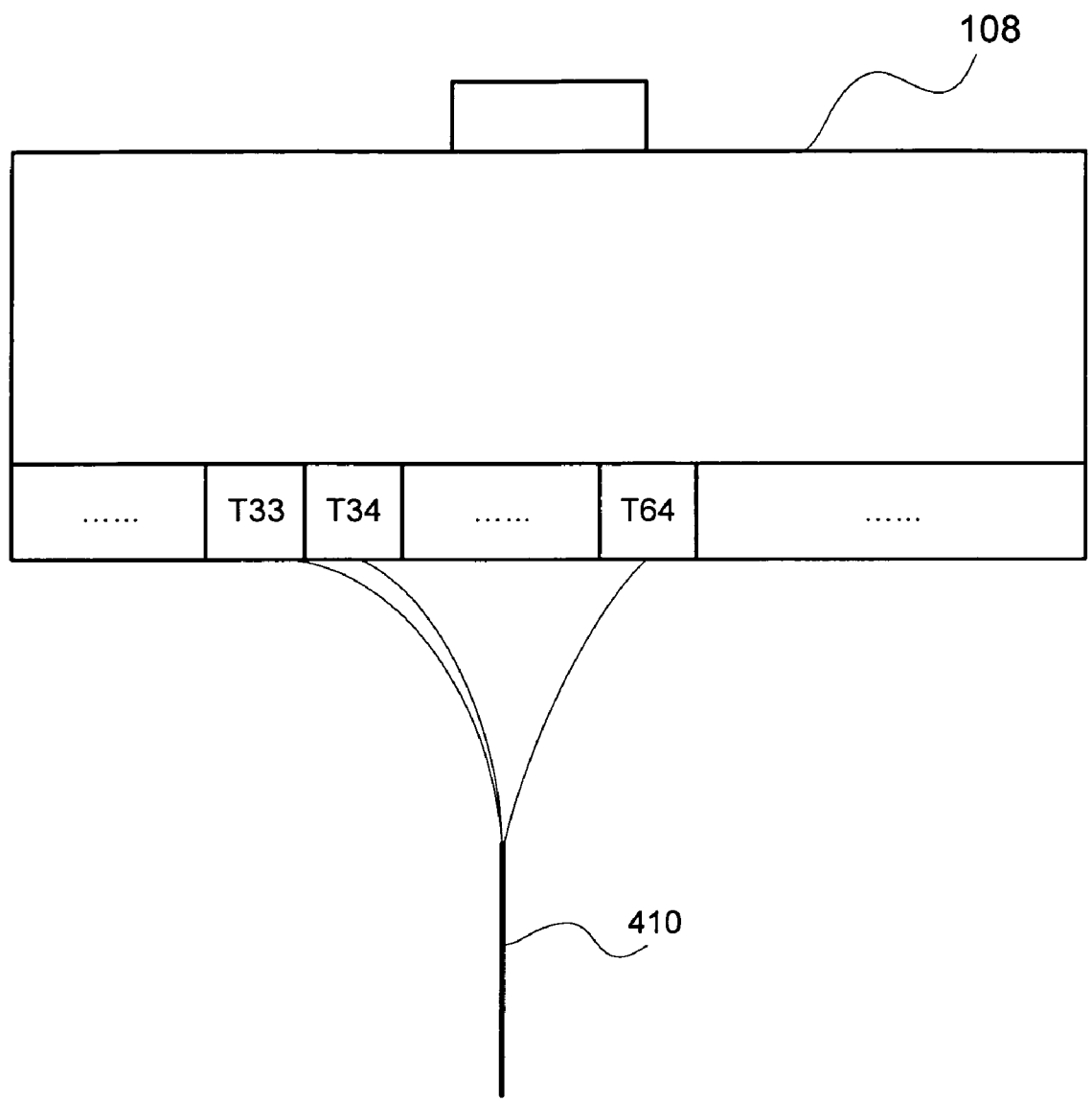
FIG. 4 shows an example for generating a high frame rate ultrasound signal.

As shown in FIG. 4, a desired location is selected to form an M-mode image. Then, a subset of transducers is selected to generate and focus the ultrasound signals. For instance, transducers T33 to T64 (32 transducers) are selected to focus the ultrasound signals for form transient M-mode (Please note that the present invention does not limit the number of ultrasound transducers to perform M-mode). By focusing the ultrasound signals, the ultrasound scanner can transmit ultrasound signals at a high frame rate. Hence, a high frame rate ultrasound signal 410 can be generated.

Figure 7B:
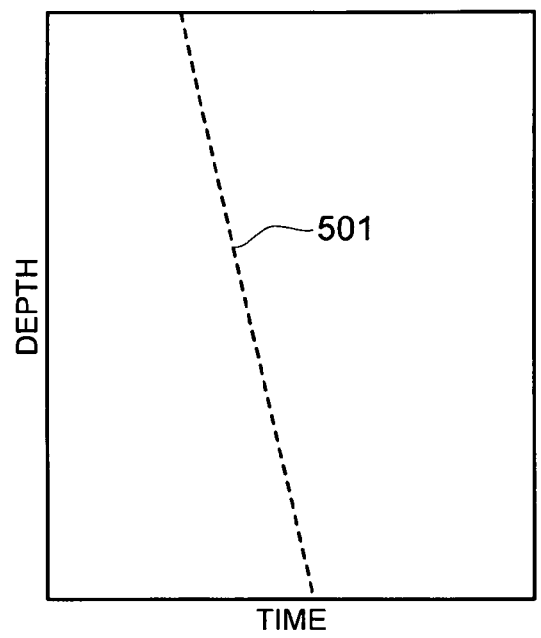
FIG. 7B shows an enhanced image of the shear wave propagation trace according to an embodiment of the present invention.

In step S506, based on a sequence of RF ultrasound data, a transient M-mode image may be formed as shown in FIG. 7A. FIG. 7A is an exemplary result of transient M-mode collected under 6000 frames/s of A-mode ultrasound signal based on RF data. The Y-axis of 7A represents the depth of the tissue and X-axis of FIG. 7A represents the time when the signal is collected. FIG. 7B is an enhanced image for shear wave propagation trace (step S507). Next, in step S508, a dashed line 701 is manually or automatically drawn that indicates the slope of the trace, which may be overlaid in the transient M-mode image of FIG. 7A. In addition to calculating the overall slope of the trace, the slopes can also be calculated for each sub-segment of the trace so as to get the slope profile along the depth direction. This profile can be coded with grey level or color scale and overlaid in the B-mode or M-mode image.

In step S509, the ultrasound system 100 calculates the elasticity measurement (Young's modulus) of the transient M-mode scan and display the result on display unit 107 in step S510. If more scanning is needed, the process returns to step S501. Otherwise, the process ends.

Figure 6:
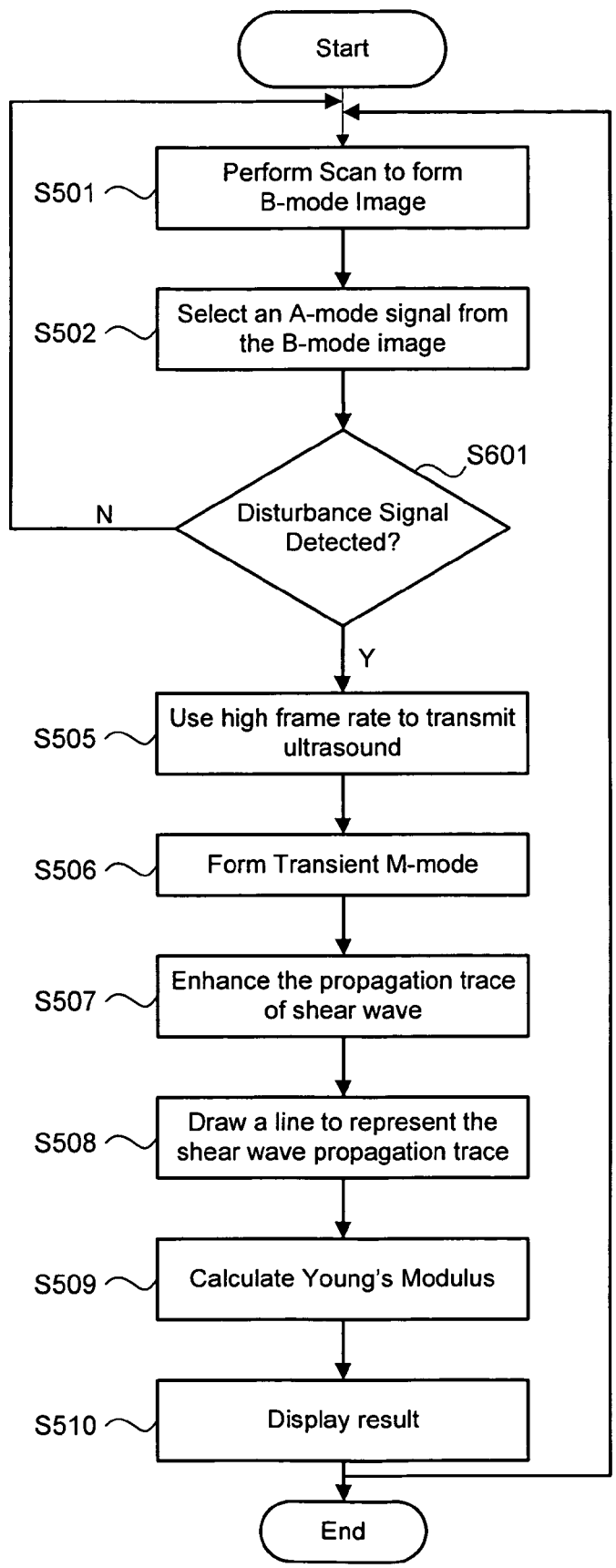
FIG. 6 shows an exemplary flow diagram for simultaneously displaying B-mode and transient M-mode ultrasound images in a case where the disturbance source is not controllable.

FIG. 6 shows an exemplary flow diagram for displaying B-mode and transient M-mode ultrasound images in a case where disturbance source is not controllable. Steps S501, S502, and S505 to S510 are the same as that described in FIG. 5. As such, the description thereof is omitted. Step S601 determines whether a disturbance signal is detected. In a case where a disturbance signal is not detected, the process returns to step S501. On the other hand, in a case where a disturbance signal is detected, the process proceeds to step S505. The trigger signal to start M-mode scanning is collected from the signal related to the disturbance, which can be ECG signal, heart pulsation, acceleration signal collected from tissue surface by an accelerometer, etc.

The present invention can provide a storage medium storing program code for performing the above-described processes to a computer system or apparatus (e.g., a personal computer), reading the program code, by a CPU or MPU of the computer system or apparatus, from the storage medium, then executing the program.

Figure 8:
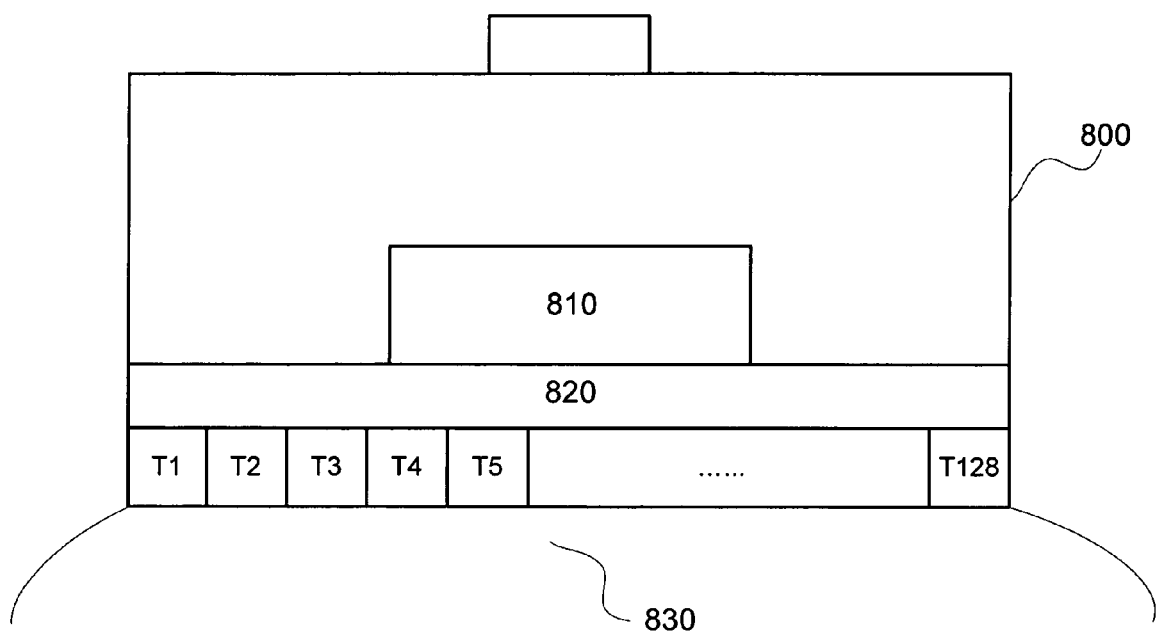
FIG. 8 is an exemplary configuration of the ultrasound probe according to an embodiment of the present invention.

FIG. 8. illustrates another embodiment of the present invention. In this embodiment, an array ultrasound probe 800 includes a vibrator 810 stored inside an ultrasound probe. It is fixed onto the backing materials or damping materials (820) behind the ultrasound transducer elements (T1 to T128) to apply vibration to tissues 830, which is in contact with the probe surface. The vibrator is driven by a pulser, which is triggered by the trigging signal from the ultrasound scanner.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A method for performing ultrasound imaging and elasticity measurement, the method comprising:
    scanning an object to obtain a B-mode ultrasound image;
    selecting an A-mode signal location from the B-mode ultrasound image;
    transmitting a high frame rate ultrasound signal, by a selected group of ultrasound transducers, at the selected A-mode signal location;
    forming a transient M-mode image based on the high frame rate ultrasound signal;
    obtaining a propagation trace of a shear wave on the transient M-mode image;
    calculating a propagation speed of the shear wave based on the propagation trace, and calculating an elasticity of the object based on the propagation speed of the shear wave; and
    displaying, simultaneously, the B-mode ultrasound image, the transient M-mode image, and the elasticity of the object.

2. The method according to claim 1, further includes synchronizing the beginning of a disturbance on the object and the forming of the transient M-mode image.

3. The method according to claim 1, wherein the high frame rate ultrasound signal is at least 1000 frames/sec.

4. The method according to claim 1, wherein the propagation trace of the shear wave is overlaid on the transient M-mode image.

5. The method according to claim 1, wherein the calculating of a propagation speed of the shear wave is based on a slope of the propagation trace of the shear wave.

6. The method according to claim 1, wherein sub-segments of the propagation trace of the shear wave are used to calculate more than one slope.

7. The method according to claim 1, further comprises selecting at least one other A-mode signal location from the B-mode image, and calculating an elasticity of the object based on a propagation speed of a shear wave for the at least one other A-mode signal location.

8. The method according to claim 5, further comprising deriving a map of Young's modulus based on the slope.

9. An imaging apparatus for performing ultrasound imaging and elasticity measurement, comprising:
    a scan control unit configured to scan an object to obtain a B-mode ultrasound image;
    a selecting unit configured to select an A-mode signal location from the B-mode ultrasound image;
    an ultrasound probe configured to transmit a high frame rate ultrasound signal, by a selected group of ultrasound transducers, at the selected A-mode signal location;
    a processing unit configured to form a transient M-mode image based on the high frame rate ultrasound signal, and to obtain a propagation trace of a shear wave on the transient M-mode image;
    a calculating unit configured to calculate a propagation speed of the shear wave based on the propagation trace, and to calculate an elasticity of the object based on the propagation speed of the shear wave; and
    a display unit configured to display, simultaneously, the B-mode ultrasound image, the transient M-mode image, and the elasticity of the object.

10. The imaging apparatus according to claim 9, wherein the ultrasound probe further includes an array of ultrasound elements and a vibrator installed inside the ultrasound probe, which is attached on a backing material of the array of ultrasound elements to apply vibration to the object,
    wherein the object is in contact with a surface of the ultrasound probe.

* * * * *